(12) United States Patent
Bird

(10) Patent No.: US 6,581,600 B2
(45) Date of Patent: Jun. 24, 2003

(54) INTERFACE APPARATUS AND COMBINATION AND METHOD

(76) Inventor: Forrest M. Bird, 1655 Glengary Bay Rd., Sandpoint, ID (US) 83864

( * ) Notice: Subject to any disclaimer, the term of this patent is extended or adjusted under 35 U.S.C. 154(b) by 0 days.

(21) Appl. No.: 09/905,480

(22) Filed: Jul. 13, 2001

(65) Prior Publication Data

US 2003/0010344 A1 Jan. 16, 2003

(51) Int. Cl.[7] ............................. A61M 15/00; A62B 9/02
(52) U.S. Cl. ............................. 128/205.24; 128/203.12; 128/912
(58) Field of Search ....................... 128/205.24, 203.12, 128/912

(56) References Cited

U.S. PATENT DOCUMENTS

| 4,592,349 A | * | 6/1986 | Bird | 128/204.25 |
| 4,694,825 A | * | 9/1987 | Slemmer et al. | 128/205.24 |
| 5,522,381 A | * | 6/1996 | Olsson et al. | 128/203.12 |
| 5,871,009 A | * | 2/1999 | Rydgren et al. | 128/203.12 |
| 6,306,099 B1 | * | 10/2001 | Morris | 600/529 |
| 6,394,092 B1 | * | 5/2002 | Barrett et al. | 128/207.17 |

* cited by examiner

*Primary Examiner*—Henry Bennett
*Assistant Examiner*—Alfred Basichas
(74) *Attorney, Agent, or Firm*—Dorsey & Whitney LLP

(57) ABSTRACT

Interface apparatus for use by a patient having a patient airway and for use with a mechanical ventilator having inspiratory and expiratory tubing. An intrapulmonary percussive ventilator having an output and an injection device coupled to the output of the intrapulmonary percussive ventilator and having an output. The interface apparatus comprises a mixing device having a mixing chamber therein and having an outlet adapted to be connected to the patient airway. The body has fittings in communication with the mixing chamber adapted to be connected to the inspiratory tubing and to the expiratory tubing of the mechanical ventilator. The body also has an injection port in communication with the mixing chamber adapted to be connected to the output of the injection device.

14 Claims, 2 Drawing Sheets

INTERFACE APPARATUS AND COMBINATION AND METHOD

This invention relates to an interface apparatus for use with a continuous mechanical volume ventilator and an intrapulmonary percussive ventilator and combination thereof and method.

It is well known that it is necessary to employ mechanical pulmonary assistance or control to support life in many situations. However, it has recently come to the attention of the medical field that there is an increasing incidence of major life-threatening barotrauma within the patient population receiving such cardiopulmonary assistance. Much of the blame on such barotrauma has been focused upon the abrupt dissecting phasic intrapulomary deliveries of programmed tidal exchanges delivered with major proximal/distal pressure gradients into the pulmonary structures of the patient. Clinical remedies for this barotrauma have been directed towards decreasing the programmed tidal volume delivery with an associated decrease in the inspiratory flow rate. Additionally suggestions have been made that the lungs of the patient should be stabilized with continuous positive end expiratory pressure to prevent peripheral (small) airway collapse, following each successive lung re-inflation associated with each tidal delivery (breath). In connection with such barotrauma it has been believed that peripheral intra-airway abrasion has been caused by the unrelenting tidal induced closure and re-inflation of small terminal pulmonary airways (which closed during the expiratory phase of the continuous mechanical ventilation); as the dilating inspiratory intrapulmonary pressure rises decayed during the expiratory phase of the mechanical ventilation, only to again be re-expanded during the next inspiratory tidal delivery. This abrasive opening and closing can occur as frequently as 18,000 times per day. Such mechanically induced lung damage required increasing oxygen concentrations in addition to the continuous mechanical ventilatory programming, which increases the onset of respiratory distress syndromes in both infant and adult patients receiving cardiopulmonary care. In addition it has been found that the reduction of tidal volumes to overcome barotrauma has increased the incidence of atelectasis and hypo-ventilation almost directly in proportion to the decrease in tidal volume delivery.

Ventilators are available which provide volumetric diffusive respiration which resolve most if not all of the ventillary compromises hereinbefore described causing barotrauma. However, there are many volume/pressure ventilators presently in service which do not have such capabilities and which represent major capital investments by hospitals and other medical facilities. There is therefore a need for an apparatus and method which makes it possible to utilize these volume/pressure ventilators now in the field to overcome or substantially eliminate the incidence of life-threatening barotrauma in patients receiving mechanical cardiopulmonary assistance.

In general, it is an object of the present invention to provide an interface apparatus for use with volume/pressure ventilators now in the field and an intrapulmonary percussive ventilator to overcome or substantially decrease the incidence of major life-threatening barotrauma in patients receiving mechanical cardiopulmonary assistance and a combination thereof and a method for managing such cardiopulmonary assistance of patients.

Another object of the invention is to provide an interface apparatus of the above character which can be readily integrated with existing volume/pressure ventilators.

Another object of the invention is to provide an interface apparatus and a combination incorporating the same which can be readily integrated with commercially available accessories.

Another object of the invention is to provide an interface apparatus of the above character which can be economically manufactured.

Additional objects and features of the invention will appear from the following description in which the preferred embodiment is set forth in detail in conjunction with the accompanying drawings.

In general, the interface apparatus of the present invention is for use with a continuous mechanical volume ventilator and an intrapulmonary percussive ventilator in which the mechanical volume ventilator is provided with an inspiratory port and an expiratory port and in which the interface apparatus is comprised of a mixing device having a body with a chamber therein and having an outlet adapted to be connected to the patient airway. The body has a fitting adapted to be connected to the inspiratory port of the mechanical volume ventilator and a fitting adapted to be connected to the expiratory port of the mechanical volume ventilator. The body is also provided with a fitting which is adapted to be connected to the intrapulmonary percussive ventilator.

Figure 1:
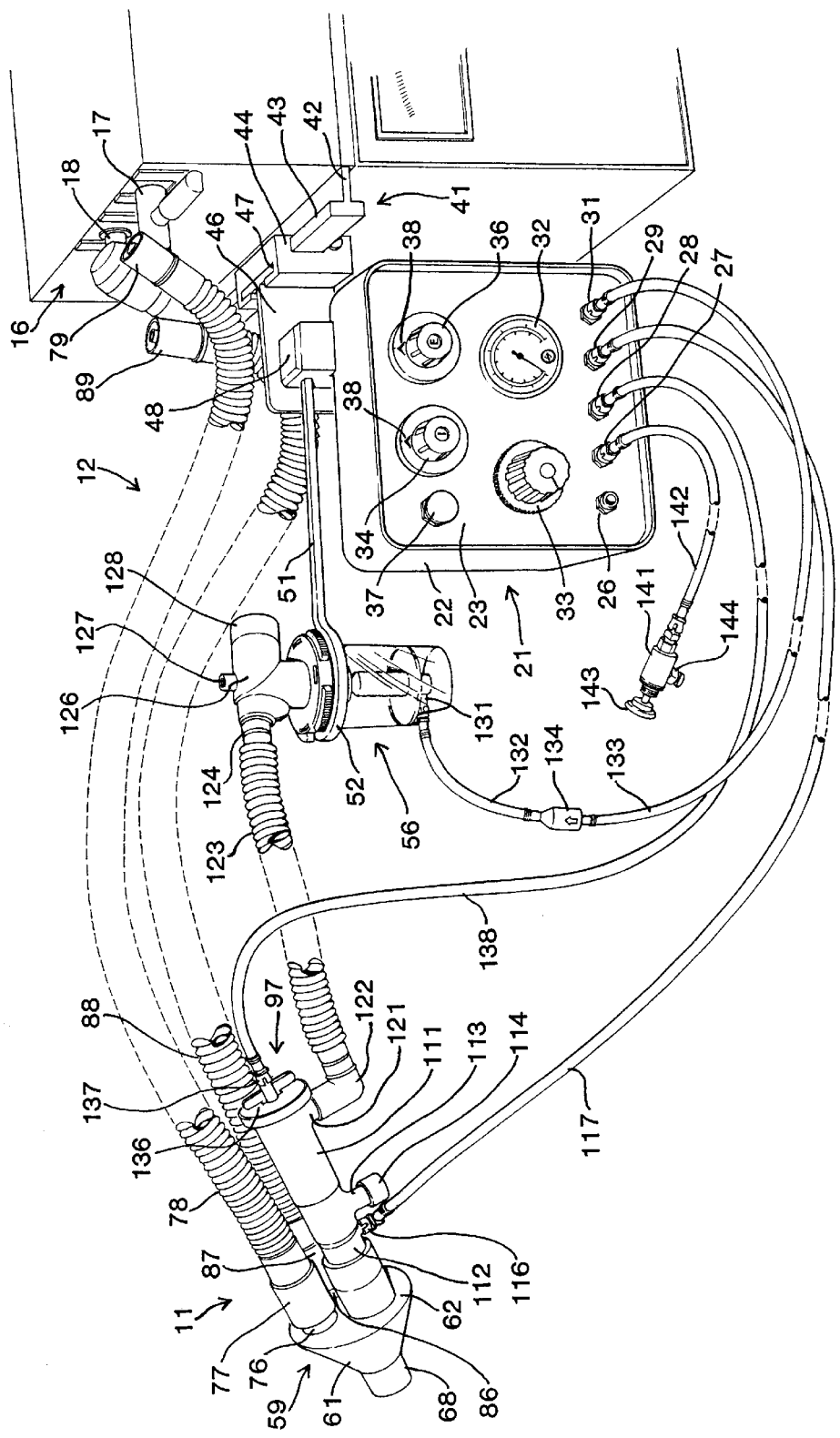
FIG. 1 is an isometric view of an interface apparatus and a combination using the same and incorporating the present invention.

More in particular as shown in FIG. 1 of the drawings, the interface apparatus 11 and the combination 12 incorporating the same is shown in FIG. 1 and consists of a conventional mechanical ventilator 16 which can be either volume oriented or pressure oriented and which is provided with an inspiratory port 17 and an expiratory port 18. The combination 12 also includes an intrapulmonary percussive ventilator 21 which is provided with a case 22 having a front panel 23 and having a plurality of fittings provided on the lower extremity of the front panel. These fittings include from left to right a source gas fitting 26, a remote fitting 27, a Phasitron® fitting 28, a gauge fitting 29 and a nebulizer fitting 31. There is also provided on the front panel a pressure gauge 32. A pressure control knob 33 is also mounted on the front panel as well as an inspiratory time increase knob 34 and an expiratory time increase control knob 36 and a manually operated inspiratory push button 37. The knobs 34 and 36 are provided with arrows 38.

The intrapulmonary percussive ventilator 21 can be of a suitable type such as the IPV-1 percussionators supplied by Percussionaire Corporation of Sandpoint Id. 83864, which provide percussive high frequency modulation of convective tidal volumes and PEEP.

In order to facilitate use of the combination 12, it may be desirable as shown in FIG. 1 to provide a bracket-type mounting assembly 41 which consists of a plate 42 lying in a horizontal plane and underlying the ventilator 16. A bar 43 which is rectangular in cross section supported by the front end of the plate 42. A slider 44 is mounted on the bar 43 in adjustable positions. A tee-shaped adapter plate 46 is mounted in a slot 47 provided in the adapter plate 46. A mounting block 48 is secured to the adapter plate 46 and is secured to the rear of the case 22 of the intrapulmonary percussive ventilator 21 so that it is supported in elevated position with respect to the case 22 and is readily accessible for operation of the controls provided on the front panel 23 hereinbefore described.

A support arm 51 is also provided on the mounting block 48 and extends outwardly therefrom and is provided with a circular distal portion 52 which removably receives a nebulizer 56 hereinafter described which also forms a part of the combination 12.

Figure 3:
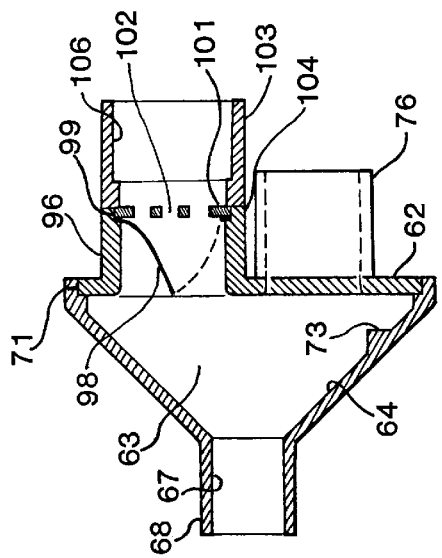
FIG. 3 is a cross sectional view of the mixing device show in FIGS. 1 and 2.
Figure 2:
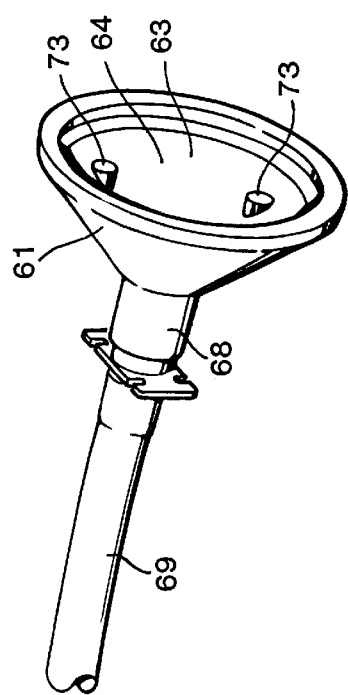
FIG. 2 is an isometric view of the mixing device utilized in the interface apparatus with the face plate or cover removed.

The interface apparatus 11 as shown in FIGS. 1, 2 and 3 consists of mixing device 59 which includes body 61 that is generally in the form of a truncated or funnel-shaped cone and includes a three-part turret or base plate 62 that forms the base of the truncated cone. The body 61 is provided with a cone-shaped mixing chamber 63 formed by a smooth conical wall 64 that adjoins and empties into a cylindrical passageway 67 provided in a cylindrical outlet 68 formed as a part of the body 61. A patient adapter 69 (see FIG. 2) of a suitable type such as an indwelling catheter is mounted on the outlet 68 and makes connection to the airway of the patient as hereinafter described. The circular base plate 62 is seated within an annular recess 71 provided in the body 61 and is fused therein. A pair of raised cylindrical molding ejection pins spaced diametrically apart are provided within the mixing chamber 63.

The flat three-part turret or base plate 62 is provided with a protruding inspiratory fitting 76 which is cylindrical in shape and opens into the mixing chamber 63. A coupling 77 is provided which mates with the inspiratory fitting 76. The fitting 76 is connected to flexible inspiratory tubing 78 that is connected to a coupling 79 that is connected to the inspiratory port 17 of the mechanical ventilator 16. The base plate 62 is also provided with a protruding expiratory fitting 86 spaced apart from the inspiratory fitting 76 which is cylindrical in shape and which has connected thereto a coupling 87 that is connected to expiratory tubing 88. The expiratory tubing 88 is connected to a coupling 89 which is connected to the expiratory port 18 of the mechanical ventilator 16.

As can be seen, the inspiratory fitting 76 and the expiratory fitting 86 form first and second fittings for the base plate 62 and are in communication with the mixing chamber 63. A third protruding fitting 96 also in communication with the mixing chamber 63 and of a larger diameter than fittings 76 and 86 is provided on the base plate 62 and extends parallel to the fittings 76 and 86 and is provided for receiving the output of a Phasitron® 97 of the type described in U.S. Pat. No. 5,116,088. The fitting 96 is provided with an isolation check valve 98 in the form of a flapper valve. The flapper valve 98 can be formed of a suitable material such as an elastomeric and is movable between open and closed positions as shown in FIG. 3. The flapper valve 98 is seated in an annular recess 99 in the cylindrical fitting 96 and is retained therein by a circular disc 101 which is provided with openings 102 therein. The fitting 96 also includes a second part 103 which is secured to a base portion 104 by suitable means such as an adhesive (not shown) so that the flapper valve 98 and the disc 101 are firmly secured between the part 103 and the portion 104. The part 103 is provided with an annular recess 106 for receiving the gases supplied by an injection device such as a Phasitron® 97.

The Phasitron® 97 as described in FIG. 1 and described in U.S. Pat. No. 5,116,088 is provided with a body 111 which is provided with an outlet 112 which is adapted to seat in the recess 106 provided in the part 103. The body 111 is also provided with an expiratory port 113 which is closed with a cap 114. The body 111 is also provided with an airway pressure monitoring fitting 116 which is connected by tubing 117 to the gauge fitting 29 on the ventilator 21. The body 111 is provided with an entrainment port 121 that has an elbow type coupling 122 mounted thereon. The coupling 122 is connected to aerosol entrainment tubing 123. The tubing 123 is connected to a coupling 124 which is mounted on a tee-shaped outlet 126 provided as a part of the nebulizer 56. The outlet 126 is provided with an IV port 127 which can be utilized for delivering drugs, etc., to the patient. The outlet is provided with an entrainment port 128.

The nebulizer 56 is of the type described in U.S. Pat. No. 4,592,349. The nebulizer 56 is provided with an inlet fitting 131 which is connected to tubing 132 that is connected to tubing 133 through a one-way check valve 134. The tubing 133 is connected to the Phasitron® fitting 31 of the ventilator 21.

The Phasitron® 97 is provided with a cap 136 removably mounted thereon which is provided with a fitting 137 that is connected to Phasitron® servo tubing 138. The tubing 138 is connected to the Phasitron® fitting 28 provided on the ventilator 21.

The interface apparatus 11 also includes a conventional manual normally closed cycling valve 141 connected by tubing 142 to the remote fitting of the ventilator 21. The manual cycling valve 141 includes a spring loaded thrust push button 143 and is provided with an outlet 144. With this valve 141 it is possible to control percussion during any segment of the tidal delivery cycle hereinafter described whether inspiratory or expiratory.

Operation and use of the interface apparatus 11 in the combination 12 in performing the method of the present invention may now be briefly described as follows. Let it be assumed that the patient adapter 69 (FIG. 2) is an indwelling airway catheter in the form of an endotracheal tube. The mechanical ventilator 16 is programmed to meet the needs of the patient depending upon the size of the patient and the medical condition of the patient to achieve the greatest level of efficacy with respect to oxygen concentrations, tidal volumes and blood gases in the patient. In conjunction therewith, a positive end expiratory pressure (PEEP) can be utilized if desired to place an expiratory pressure against the lung of the patient. Thus, by way of example for a patient sick with cardiopulmonary disease, the pressure control knob 33 on the ventilator 21 is adjusted to provide 40 pounds of pressure to the lungs of the patient as indicated by the gauge 32. Ventilatory gases are supplied by the ventilator 16 to cause sinusoidal ventilation of the lungs of the patient with tidal volumes at a frequency rate of 5 to 50 breaths per minute. Rapid or high frequency tidal volumes at a frequency rate of 100 to 750 breaths per minute are superimposed upon the ventilatory carrier waves supplied by the ventilator 16. In effect what is occurring, the carrier wave generated by the mechanical ventilator 16 is modulated with the higher frequency percussive waves produced by the ventilator 21. As soon as this occurs, there is an increase in the blood gas interface to make it possible to reduce the peak pressure being supplied by the ventilator 16 which is the ventilator which typically is barotraumatic to the lungs of the patient. As the patient begins to improve because of this increased blood gas interface, with the consequent reduction in peak pressures provided by the ventilator 16, it is possible to reduce oxygen concentrations to inhibit oxygen toxicity. In other words in accordance with the present invention by utilizing intrapulmonary percussive ventilation to modulate the output from the mechanical ventilator it is possible to gradually reduce the pressure of the gases being supplied by the mechanical ventilator as well as reducing oxygen concentration in the lungs of the patient.

Figure 4:
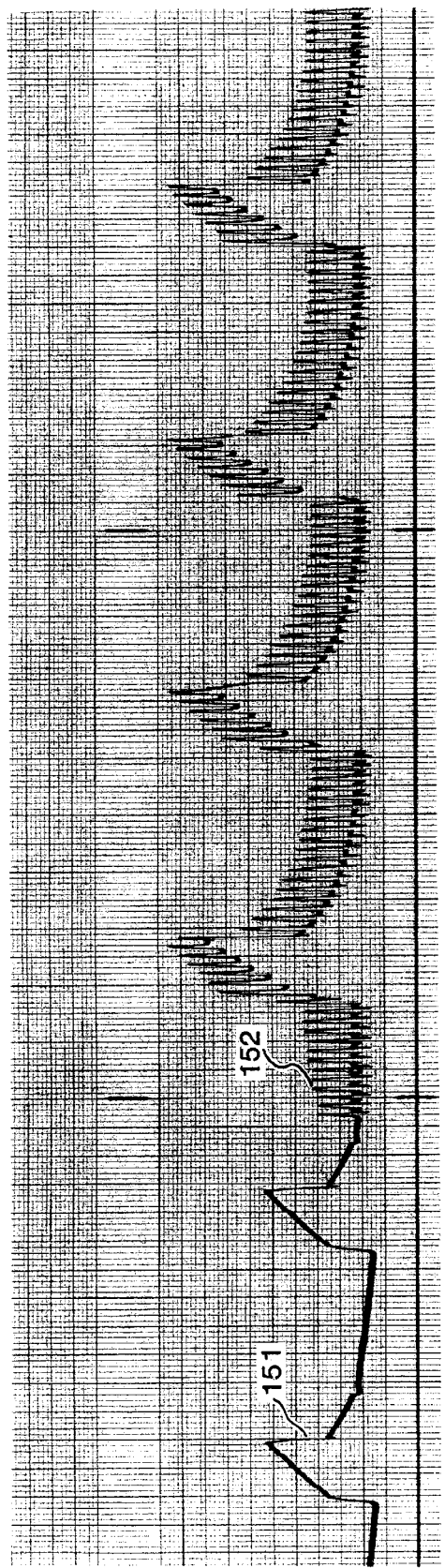
FIG. 4 is a graph showing the manner in which percussive endobronchial deliveries are modulating a proximal airway pressure wave carrier utilizing the present invention.

A demonstration of the operation of the interface apparatus 11 in a combination 12 in accordance with the present invention is shown in FIG. 4. There is shown a low frequency waveform 151 which represents the low frequency tidal volumes delivered to the airway of the patient by the mechanical ventilator 16 upon which there is delivered high frequency tidal volumes represented by the waveform 152 modulating the waveform 151 supplied by the intrapulmonary percussive ventilator 21 to the airway of a theoretical patient represented by a Michigan Lung Model 600. The low frequency waveform was produced by a constant volume mechanical Servo C ventilator supplied by Siemens and the high frequency waveform was produced by an intrapulmonary percussive ventilator IPV-1S supplied by Percussionaire Corporation of Sandpoint, Id., in combination with an interface apparatus of the present invention. Utilizing this combination as shown by the curves 151 and 152 in FIG. 4, percussive endobronchial deliveries were supplied by the percussion ventilator modulating a proximal airway pressure wave carrier created by the mechanical ventilator and utilizing the interface apparatus of the present invention to the lung model which had a static compliance of 0.02 liters per cm of $H_2O$ with a resistance of 24.59 cm $H_2O$ liters per second. The servo cycling rate for the Siemens mechanical ventilator was 14 breaths per minute. The Percussionaire intrapulmonary percussive ventilator had a cycling rate of 346 breaths per minute. The mechanical ventilator produced tidal volumes of 750 milliliters at the rate of 14 breaths per minute. The Percussionaire intrapulmonary percussive ventilator supplied the modulated subtidal volumes at 10 milliliters. Thus the ventilation provided to the lung model by the mechanical ventilator was 9.8 liters per minute. The total tidal volumes supplied by the mechanical ventilator as augmented by the modulation of the carrier wave with intrapulmonary percussive ventilation produced a total tidal output of 44.0 liters per minute. The post inspiratory pressure of the mechanical ventilator was 32 cm $H_2O$ which increased to 55 cm of $H_2O$ when modulated with the intrapulmonary percussive ventilation. The pressure rise for the mechanical ventilator was 32 cm of $H_2O$ and when modulated with intrapulmonary percussive ventilation produced a pressure rise of 55 cm $H_2O$.

From the foregoing it can be seen that large tidal volumes can be delivered to the lungs of a patient without creating any significant barotrauma by modulating the low frequency tidal volumes with high frequency tidal volumes to progressively tap inflate and deflate the lungs of the patient.

The cone-shaped mixing device 59 can also be identified as an interfacing funnel which is substituted for the conventional Y piece at the patient's proximal airway. This mixing device serves as a conic manifold and provides a flat top cone-shaped mixing chamber 63 that serves as means for providing inspiratory tidal volumes to the lungs of the patient. Exhaled gases from the lungs of the patient backflow through the cone-shaped mixing chamber 63 and into the expiration tubing 88 into the exhalation valve of the ventilator 16. During the inspiratory phase of the ventilator 16, this exhalation valve is closed, preventing outflow from the breathing circuit as inspiratory pressurization occurs. During exhalation of the patient, the directionally gated inspiratory tubing prevents backflow through the inspiratory tubing into the ventilator 16. The parallel inspiratory and expiratory tubing 78 and 88 connected side by side into the base plate 62.

Condensational water trapping within the top margins of the funnel-shaped or cone-shaped mixing chamber 63 is minimized while still permitting conventional back draining through the tubing of the breathing circuits into their respective water traps (not shown). The large percussion port or fitting 96 carried by the mixing device 59 and connected to the Phasitron® makes it possible to introduce into the mixing chamber 63 periodic high velocity impulse injected inflow generated by the venturi within the Phasitron® to be injected into the outlet 67 of the mixing device 59 with minimal deflective angulation because of the cone-shaped surface of the mixing chamber.

The directional flapper valve 98 by being hinged at the outer rim of the funnel of the mixing device 59 serves to direct the percussive outflow from the venturi of the Phasitron® 97 toward the central neck of the cone-shaped mixing chamber 63. Linear alignment of the output from the Phasitron® 97 with the outlet 67 serves to maximize the injection forces of the mixed gases against the pulmonary airways of the patient by minimizing non-elastic frictional forces. The ventilator 21 generates intrapulmonary wedge pressures which are superimposed upon and modulate the output from the mechanical ventilator 16.

In the treatment of a patient it has been found desirable to utilize the expiratory control knob 36 to increase the functional residual capacity in the lungs of the patient which can be defined as the amount of gas in the lungs of the patient at the time the next inspiratory interval arrives. By shortening up the expiratory time, there is insufficient time for the lungs of the patient to empty by the patient breathing out. The inspiratory phase is then commenced to bring the lungs of the patient up to the desired capacity and thereby actually control the volume of gases in the lungs. Thus this knob 36 facilitates the blood gas interface while making it possible to keep the lowest pressures with the maximum clinical efficacy.

It has been found by utilizing this interface apparatus in combination with the mechanical ventilator 16 and the intrapulmonary percussive ventilator 21, it is possible to decrease the severe tidal pressure rises and the oxygen concentrations within a minute or so after commencement of treatment of the patient suffering with cardiopulmonary disease.

The interface apparatus 11 in operating in the combination in which the mixing chamber 63 of the body 61 is in communication with both the inspiratory tubing 78 and the expiratory tubing 88 makes it possible for the mechanical ventilator 16 to continue to operate even if the intrapulmonary percussive ventilator 21 is not operating. This is made possible because the third port or fitting 96 connected to the Phasitron® 97 is provided with the flapper valve 98 which only permits gases to go into the mixing chamber 66 and not pass out through the port or fitting 96.

Although the inspiratory tubing 78 and the expiratory tubing 88 are color coded and are placed on the appropriate fittings, they can be interchanged without deleterious effects on the operation of the apparatus because both are in communication with the mixing chamber 63. The flapper valve 98 isolates any gas pressure within the mixing chamber 63 from outside ambient pressure because the flapper valve 98 only opens inwardly. With the Phasitron® 97 connected to the fitting 96, when the pressure of the gas supplied by the Phasitron® is greater than the pressure in the mixing chamber 63, the flapper valve 98 opens and delivers the gas to the patient by delivering the same into the mixing chamber 63 and thence through the outlet 68 to the patient adapter 69. As soon as exhalation begins to occur, the flapper valve 98 closes. Thus it can be seen that as soon as the Phasitron® 97 is dynamically active, the flapper valve 98 opens and closes under the control of the ventilator 22. During injection of gas from the Phasitron® 97, there is a pressure build-up because of the clutching action occurring in the Phasitron® 97. The Phasitron® 97 as it is used in the combination of the present invention is only utilized as an injector. Exhaust gases from the lungs of the patient do not come back through the Phasitron® 97 but rather go back through the exhalation port of the ventilator 16. For this reason the expiration port 113 of the Phasitron® is closed by the cap 114. By capping off the expiratory port 113 of the Phasitron® the entire combination operates more quietly.

The manual cycling valve 141 which serves as a remote switch makes it possible to manually control the length of the inspiratory phase and the expiratory phase. This makes it possible during this manual cycling to actually observe the operation of the lungs of the patient during manual pacing. The manual push button 37 provided on the ventilator 21 when depressed causes the ventilator 21 to supply a constant flow of gas through the Phasitron® 97.

The mixing chamber 63 has been kept very small as approximately 26 to 27 cc's of space to minimize rebreathing of exhaled gases. In addition to mixing of the gases provided by the ventilators 16 and 21 in the mixing chamber 63, the mixing chamber 63 also serves to mix therein the aerosol being supplied from the nebulizer 56. The aerosol can be in the form of a medicated aerosol, saline or water. When a medicated aerosol is desired, the pharmaceutical can be introduced through the IV port 127. In this way particles of a pharmaceutical such as a vasoconstrictor or a bronchodilator are injected into the mixing chamber 63 where they are introduced into the modulated gases in the mixing chamber.

When the venturi within the Phasitron® 97 is energized during a percussive subtidal delivery the pressure within the venturi entrainment port of the Phasitron® 97 becomes subambient. The aspirational pressure drop within the entrainment port of the Phasitron® 97 provides the capability of aspirating a dense aerosol concentration from the aerosol entrainment tubing 123 for ultimate injection into the pulmonary airways of the patient. The aerosol entrainment tubing 123 is connected to the outlet of the nebulizer 56. The nebulizer provides a constant flow which is vented to ambient with a non-directional hinged gate and opens in either direction with a pressure differential of less than 5 cm of $H_2O$. Venting this constant flow of the nebulizer 56 to ambient permits capping off of the exhalation port of the Phasitron® 97 with the cap 114 to thereby eliminate a major source of high velocity air flow noise. In the combination 12, the mechanical ventilator 16 typically provides monitoring and failure alarming for the combination 12. Should the ventilator 21 fail for some reason, the patient will still be ventilated with the programmed tidal exchange from the ventilator 16. Should the mechanical ventilator 16 fail, the patient will be ventilated with a programmed oscillatory demand continuous positive airway pressure from the ventilator 21 which can be overridden by a patient's spontaneous breathing. Typically the mechanical ventilator 16 can provide traditional continuous humidification of its tidal volume deliveries. In the present combination 12, the ventilator 21 in combination with the nebulizer 56 delivers bulk aerosolized wetting agents as well as pharmaceuticals for endobronchial delivery to facilitate the elimination of airway secretions in the patient. The ventilator 21 has the capability to selectively adjust the time between each percussive subtidal intrapulmonary delivery to control dynamic functional residual lung volume. The adjustable or variable i/e ratio, which also can be termed percussive i/e ratio, provided by the knobs 34 and 36 of the ventilator 21 enables precise control over the dynamic functional residual capacity which can be defined as the amount of air left within the lungs at the start of the next inspiratory inflation. The level of residual lung inflation is determined by how much pressure is left within the primary lung structures (alveoli) from the last lung inflation before the next periodic reinflation commences. The less the expiratory time interval, the greater the residual air left within the lungs at the start of the next inflation because the lungs of the patient do not have time to empty. This is a selectable variable which controls inflation of the small peripheral airways of the patient with intrapulmonary wedge pressures during intrapulmonary ventilation of the patient in lieu of PEEP. Therefore during use of the ventilators 16 and 21 in the combination hereinbefore described, the degree of peripheral lung deflation is determined by the intrapulmonary wedge pressure created by the ventilator 21 in lieu of PEEP from the mechanical ventilator 16. PEEP maintains a constant expiratory pressure within the entire thoracic cage of the patient, serving to depress cardiac output as well as depressing vesicular peristalsis within the bronchial, pulmonary and lymph circulations.

From the foregoing it can be seen that the interface apparatus 11 in operation in the combination 12 makes it possible to supply to the lungs of the patient modulated gases which have the injected aerosol therein and thereby inflate the lung gradually rather than abruptly as with a conventional mechanical ventilator. By providing the modulated flow of gases to the lungs of the patient, the lungs are urged to become more compliant and provide an improved blood gas interface for an alveolar gas exchange. In other words, the present invention by providing for oscillatory percussive enhancement of existing volume constant pressure variable ventilation with intrapulmonary percussive ventilation, the barotraumatic consequences of utilizing existing volume/pressure ventilation is effectively obtunded in a typical patient. The present invention by providing a modulated gas input makes it possible to gradually inflate and deflate the lung with many subtidal volume deliveries which gradually tap inflate and deflate the elastomeric intrapulmonary structures of the lungs of the patient. The apparatus and method of the present invention makes it possible to minimize or eliminate intra-airway inflammation by inhibiting repeated small peripheral airway collapse and re-inflation without the use of post-expiratory end pressure. Peripheral airway collapse does not occur with use of the present invention because of the automatic intrapulmonary wedge pressure factored by the percussive rate and a slightly positive i/e ratio provided by the intrapulmonary percussive ventilator 21 which serves to stabilize the peripheral airways between the percussive higher frequency subtidal deliveries. Therefore, the phasic "frictional rub" within airways with diameters below 2 mm is minimized by the expiratory peripheral intrapulmonary stabilization provided by the present invention. The deleterious effects of PEEP in terms of cardiac output, are minimized by programming of the apparatus of the present invention. When PEEP is programmed, the scheduled positive end expiratory pressure (PEEP) exits continuously from the proximal airway down through the entire thoracic cage of the patient.

When the intrapulmonary percussive ventilator 21 of the present invention is programmed correctly, the automatic peripheral intrapulmonary wedge pressure is only maintained within peripheral pulmonary airways, with an ambient pressure drop of the proximal airway between each subtidal delivery. The apparatus and the method of the present invention also is an aid in creating an acute (near instantaneous) percussive pressure rise and drop within the intra-thoracic bronchial, pulmonary and lymph circulations. Thus there is created an enhanced directional fluid flow (vesicular peristalsis) through these circulations.

Also in connection with the foregoing it can be seen that the combination which includes two independent ventilators makes it possible to program a unique convective/diffusive intrapulmonary ventilation. The endobronchial percussion of the ventilator 21 can be employed to mechanically mix the intrapulmonary gases, thus creating high levels of intrapulmonary diffusion which serve to increase oxygen tensions at the blood gas interface while concomitantly diffusing carbon dioxide away from the peripheral lung (alveolar) structures. The periodic tidal exchange created by the mechanical ventilator programming serves to convectively wash out endobronchial carbon dioxide, diffusing up through the pulmonary airways from the alveolar source. Therefore by providing unique programming, the combination of the two ventilators 16 and 21 makes it possible to provide greater efficacy in the cardiopulmonary critical care patient having variable lung compliance with considerably less potential for barotrauma.

What is claimed:

1. Interface apparatus for use by a patient having a patient airway and for use with a mechanical ventilator having inspiratory and expiratory tubing, an intrapulmonary percussive ventilator having an output and an injection device coupled to the output of the intrapulmonary percussive ventilator and having an output, comprising a mixing device having a body providing a cone-shaped mixing chamber therein and having an outlet centrally disposed with respect to the cone-shaped mixing chamber for connection to the patient airway, said body having fittings in communication with the mixing chamber for connection to the inspiratory tubing and to the expiratory tubing of the mechanical ventilator, the body also having an injection port in communication with the mixing chamber for connection to the output of the injection device.

2. Interface apparatus as in claim 1 wherein said injection port has a size greater than the fittings connected to the inspiratory tubing and the expiratory tubing.

3. Interface apparatus as in claim 1 further including a one-way valve provided in the injection port.

4. Interface apparatus as in claim 3 wherein said one-way valve is in the form of a flapper valve only permitting inward flow through the injection port and preventing outward flow from the injection port.

5. Interface apparatus for use by a patient having a patient airway and for use with a mechanical ventilator having inspiratory and expiratory tubing, an intrapulmonary percussive ventilator having an output and an injection device coupled to the output of the intrapulmonary percussive ventilator and having an output, comprising a body providing a mixing device having a mixing chamber therein and having an outlet adapted to be connected to the patient airway, said body having fittings in communication with the mixing chamber and connected to the inspiratory tubing and to the expiratory tubing of the mechanical ventilator, the body also having an injection port in communication with the mixing chamber and connected to the output of the injection device, said mixing chamber in said body being in the form of a truncated conical mixing chamber, said body being provided with a flat base plate forming the base of the truncated conical mixing chamber, said outlet of the mixing chamber being centrally disposed with respect to the conical chamber.

6. Interface apparatus as in claim 5 wherein said fittings connected to the inspiratory tubing and the expiratory tubing and the injector port are mounted in the base plate.

7. A combination for use with a patient having a patient airway, a mechanical ventilator having inspiratory tubing and expiratory tubing and providing a selected tidal volume through the inspiratory tubing, an intrapulmonary percussive ventilator having an output, an injection device connected to the output of the intrapulmonary percussive ventilator and having an outlet and a mixing device coupled to the mechanical ventilator and to the intrapulmonary percussive ventilator, the mixing device comprising a body having a mixing chamber therein and having an outlet adapted to be connected to the patient airway, the body having an inspiratory port and expiratory port and an injection port in communication with the mixing chamber, means connecting the inspiratory port of the mixing device to the inspiratory tubing of the mechanical ventilator, means connecting the expiratory port of the mixing device to the expiratory tubing of the mechanical ventilator and means for coupling of the output of the injection device to the injection port of the mixing device.

8. A combination as in claim 7 further including a one-way valve disposed in the injection port of the mixing device and permitting flow into the mixing chamber from the injection port but preventing flow out of the mixing chamber through the injection port.

9. A combination as in claim 7 wherein said chamber in the mixing device is conical in shape and wherein the outlet of the mixing device is centrally disposed with respect to the conical chamber.

10. A combination as in claim 7 wherein said inspiratory port, said expiratory port and said injection port open into the mixing chamber in a common plane.

11. A combination as in claim 7 further including a nebulizer coupled to the intrapulmonary percussive ventilator and supplying aerosols to the injection device.

12. A method for supplying pulmonary gases to a patient having an airway by the use of a mechanical ventilator providing cyclic low frequency tidal volumes and an intrapulmonary percussive ventilator supplying high frequency tidal volumes, the method comprising the steps of supplying low frequency tidal volumes from the mechanical ventilator, superimposing the higher frequency tidal volumes from the intrapulmonary percussive ventilator onto the low frequency tidal volumes of the mechanical ventilator to provide modulated tidal volumes and supplying the modulated tidal volumes to the airway of the patient.

13. A method as in claim 12 further including the step of introducing aerosols into the high frequency tidal volumes.

14. A method as in claim 12 wherein the low frequency ranges from 5 to 50 breaths per minute and wherein the high frequency ranges from 100 to 750 breaths per minute.

* * * * *